United States Patent [19]
Youssefyeh et al.

[11] Patent Number: 5,968,519
[45] Date of Patent: Oct. 19, 1999

[54] METHOD FOR THE TREATMENT OF TOPICAL INFLAMMATORY DISEASES

[76] Inventors: Parvin Youssefyeh, 1175 York Ave, Apt 14D, New York, N.Y. 10021; Ronit Y. Arginteanu, 401 E. 86th St., Ninth Floor, New York, N.Y. 10028

[21] Appl. No.: 09/080,129

[22] Filed: May 15, 1998

Related U.S. Application Data

[63] Continuation-in-part of application No. 08/753,926, Dec. 3, 1996, Pat. No. 5,753,266.

[51] Int. Cl.$^6$ .............................. A61K 9/10; A61K 9/06; A61K 35/78
[52] U.S. Cl. ..................... 424/195.1; 514/825; 514/886
[58] Field of Search ........................................ 424/195.1

[56] References Cited

U.S. PATENT DOCUMENTS

| | | | |
|---|---|---|---|
| 2,978,381 | 4/1961 | Freedman et al. | |
| 3,584,129 | 6/1971 | Kitson | 514/825 |
| 4,009,290 | 2/1977 | Okumari et al. | 126/489 |
| 4,072,669 | 2/1978 | Betschart | 260/123.5 |
| 4,623,539 | 11/1986 | Tunc | 124/79 |
| 4,806,354 | 2/1989 | Green | 424/154 |
| 4,898,721 | 2/1990 | Alvey | 423/240 |
| 4,981,844 | 1/1991 | Alexander et al. | 514/21 |
| 5,063,062 | 11/1991 | Greenspan et al. | 424/443 |
| 5,162,113 | 11/1992 | Oh et al. | 424/195.1 |
| 5,397,778 | 3/1995 | Forse et al. | 514/198 |
| 5,436,386 | 7/1995 | Weisker | 800/200 |
| 5,753,266 | 5/1998 | Youssefyeh et al. | 424/484 |

FOREIGN PATENT DOCUMENTS 0392806  10/1990  European Pat. Off. .

OTHER PUBLICATIONS

C.A. 128: 200726 R.B. Zurier et al Arthritis Rheum. 41(1) 1998 163–170.
C. A. 129:280984 C. Hioki et al Sep. 8, 1998.
C. A. 95:171434 May 26, 1981 Nihon Surfactants Co. Ltd.

*Primary Examiner*—Peter F. Kulkosky
*Attorney, Agent, or Firm*—Imre Balogh

[57] ABSTRACT

Method for the treatment of inflammation and pain associated with inflammatory dermatoses, gingivitis and acute injury with a composition of finely divided powder of safflower seed or its extract contained in a pharmaceutically acceptable carrier.

13 Claims, No Drawings

METHOD FOR THE TREATMENT OF TOPICAL INFLAMMATORY DISEASES

This invention is a continuation-in-part of application Ser. No. 08/753,926 filed on Dec. 3, 1996, now U.S. Pat. No. 5,753,266.

BACKGROUND OF THE INVENTION

1. Field of the Invention

The present invention relates to treatment of mammals by reducing inflammation that triggers the onset of rheumatic diseases, eczema, urticaria, psoriasis, erythema multiforme and lichen planus; inflammation of the gums, and chronic locaized bodily pain derived from acute injury. The present invention is also directed to the treatment of delaying menopause.

2. Reported Developments

Rheumatoid arthritis (hereinafter sometimes referred to as RA) is a common type of arthritis that causes inflammation in the lining of the joints and sometimes other internal organs. RA tends to persist for many years, typically affects many different joints throughout the body, and ultimately can cause damage to cartilage, bones, tendons and ligaments. RA is a chronic, inflammatory, connective-tissue disorder affecting more than five million individuals in the U.S., and accounting for considerable disability in terms of missed work, lost wages, and reduced productivity. The disease can occur at any age, but it most commonly begins in the third to fifth decades of life.

The American College of Rheumotology has established criteria of the diagnosis of rheumatoid arthritis which include:

1. Morning stiffness lasting at least one hour;
2. Swelling of three or more joints;
3. Swelling of the wrist, metacarpophalangeal or proximal interphangeal joints;
4. Symmetric joint swelling;
5. Rheumatoid nodules;
6. Positive rheumatoid factor; and
7. Changes on hand radiographs typical of rheumatoid arthritis that must include erosions or unequivocal bony decalcification.

The correct diagnosis of RA is essential for the clinician and involves certain clinical, laboratory and radiological findings. The diagnosis is influenced by the age and sex of the patient, the pattern of joint involvement, the onset and course of the disease and extrarticular manifestations.

In contrast to rheumatoid arthritis, osteoarthritis (hereinafter sometimes referred to as OA), the illness most often contemplated in the differential diagnosis, usually begins after the age of 50 and affects men and women equally. The joints involved in OA are different from those in RA and are not necessarily symmetrically affected. In OA, joint pathology is primarily mechanical, and synovial membrane inflammation is minimal.

As pertaining to the present invention certain other inflammatory arthritis is differentiated from RA as listed in Table I.

TABLE I

Differential Diagnosis of Rheumatoid Arthritis*

Seronegative spondyloarthropathy
(ankylosing spondylitis, reiters syndrome, psoriatic arthritis, enteropathic arthritis)
Crystal-induced arthropathy
(gout, pseudogout)
Diffuse connective tissue disease
(systemic lupus erythematosus, polymyosiis, fibromyalgia)
Infectious arthritis
Osteoarthritis
Polymyalgia rheumatica
Reactive arthritis
Hemoglobinopathies
Hemachromatosis
Lyme disease
Malignancy
Thyroid disease
Hemophilic arthropathy
Hypertrophic osteoarthritis

*Adapted from Textbook of Rheumatology. Philadelphia, W. B. Saunders Co., 1989, pp 943–981

With varying clinical significance, RA can at times affect other areas of the body. The most characteristic of these so-called extra-articular manifestations are rheumatoid nodules. They can be found subcutaneously in up to 25% of rheumatoid patients, especially over extensor surfaces and in pressure areas. Common sites include the olecranon regions, fingers, Achilles tendons, the sacrum and the occiput. The presence of subcutaneous nodules is helpful diagnostically, because they are uncommon in the other forms of inflammatory arthritis. Nodules can also occur in visceral organs, including the lungs and the heart.

As discussed above, the primary cause of RA is unknown. It is thought to be triggered by the presence of an as yet unidentified antigen(s) in an immunogenetically susceptible host, and the nature of the antigen responsible for the arthritic reactions in RA has yet to be clearly established.

Heretofore medical management of RA involved three general approaches.

The first is the use of aspirin and other nonsteroidal anti-inflammatory analgesics, and low-dose glucocorticoids to control the symptoms and signs of the local inflammatory process. These agents are rapidly effective at mitigating symptoms and signs, but they appear to exert little effect on the progression of the disease.

A second group of drugs includes a variety of agents that have been classified as the disease-modifying drugs. These agents appear to have the capacity to decrease elevated levels of acute phase reactants in treated patients, and therefore, are thought to modify the destructive capacity of the disease.

The third class of agents includes the immunosuppressive and cytotoxic drugs that have bee shown to ameliorate the disease process in some patients. These last two classes of agents, however, often cause serious side effects including the development of heart and liver diseases, increase in blood pressure, blindness and malignant neoplasms.

The prior art treatment of RA is based on the following two principles: first, RA is a systemic connective-tissue disorder that is not remediable solely through local measures. Second, RA is a progressive disease that can potentially lead to severe cartilage and bone destruction, organ damage, and decreased life expectancy. Current regimens are predicated on controlling the immune system disturbance to reduce joint discomfort and destruction and this to maintain the patient's activities of daily living.

Available drug preparations for the treatment of RA include the following.

(1) NSAIDS: Nonsteroidal Anti-Inflammatory Drugs

Pharmacologic treatment of RA has advanced steadily in the past several decades, but none of the agents used so far can cure RA. Aspirin remains an important part of the treatment program for many people with RA. To be effective, it must be given in doses much higher than commonly used as an over-the-counter remedy for minor aches and pains. Compared to other similar NSAIDS, aspirin is less expensive and its blood level can be precisely measured. However, it can cause stomach problems in many people. Many physicians recommend the use of enteric (coated) forms of aspirin.

NSAIDS are a large group of drugs that have mechanisms of action similar to aspirin. Like aspirin, these medications can relieve some of the pain associated with RA temporarily. The NSAIDS are the most frequently recommended anti-rheumatic medications, and the first line of therapy in RA. As a result of the capacity of these agents to block the activity of the enzyme cyclooxygenase and therefore the production of prostaglandins, prostacyclin and thromboxames, they have analgesic, anti-inflammatory and antipyretic properties. Table II lists the most commonly prescribed NSAIDS.

TABLE II

Commonly Prescribed NSAIDS Grouped According To Their Elimination Half-Lives

| Short Acting (6 hours) | Intermediate Acting (7 to 14 hours) | Long Acting (15 hours) |
|---|---|---|
| Aspirin | Diflunisal | Azapropazone |
| Diclofenac | Naproxen | Nabumetone |
| Etodolac | Salsalate | Oxaprozin |
| Fenoprofen | Sulindac | Piroxicam |
| Flufenamic acid | | |
| Flurbiprofen | | |
| Ibuprofen | | |
| Indomethacin | | |
| Ketoprofen | | |
| Meclofenamic acid | | |
| Tolmetin | | |

Table III lists the commonly prescribed NSAIDs by classification, half-life and dosage range.

TABLE III

Commonly Prescribed NSAIDS

| Classification | Half Life, hr | Dosage Range, mg/day |
|---|---|---|
| Proprionic Acid | | |
| Ibuprofen | 2 | 1200–3200 |
| Naproxen | 13 | 250–1500 |
| Fenoprofen | 2 | 1200–3200 |
| Ketoprofen | 1.5 | 100–300 |
| Oxaprozin | 40 | 600–1800 |
| Phenylacetic Acid | | |
| Diclofenac | 1.5 | 100–150 |
| Indoleacetic Acid | | |
| Indomethacin | 3–11 | 50–200 |
| Sulindac | 16 | 300–400 |
| Tolmetin | 1–2 | 600–2000 |
| Fenamate | | |
| Meclofenamate | 2–3 | 200–400 |
| Oxicam | | |
| Piroxicam | 30–86 | 20 |

These agents are all associated with a wide spectrum of toxic side effects. A common side effect of these drugs is bleeding from the stomach. Overall dose is limited by such gastrointestinal erosions, as well as azotemia, platelet dysfunction, exacerbation of allergic rhinitis and asthma, liver function abnormalities, some renal and cardiovascular irritation, and CNS toxicity like tinnitus, although patients occasionally differ unpredictably in their response to an individual NSAID.

An individual's response to the various NSAIDS is quite variable. Gastrointestinal ulcerations develop in 0 to 30% of NSAID-treated patients. Duodenal lesions are less common than gastric ulcers. The nephrotoxic effects of NSAIDS are well documented. Several mechanisms leading to renal prostaglandin synthesis may adversely affect renal blood flow and in certain situations, lead to acute insufficiency. At high risk are patients with minor or major pre-existing changes in renal function, such as those with changes related to aging, diabetes mellitus, hypertension, congestive heart failure, use of diuretics or low salt diet, cirrhosis, and chronic renal failure of any other cause.

Once the diagnosis of rheumatoid arthritis has been firmly established as an insufficient response to local measures and NSAIDS determined, the addition of DMARDs (disease modifying antirheumatic drugs) to the regimen is normally considered. These drugs include gold compounds, penicillamine, hydroxychloroquine, methotrexate and aza-thioprine. Estimated rates of efficacy and toxicity of these remittive agents is shown in Table IV.

TABLE IV

Estimated Rates of Efficacy and Toxicity of Remittive Agents

| TOXICITY | EFFICACY High | EFFICACY Intermediate |
|---|---|---|
| High | Cyclophosphamide | Azathioprine |
| | Parenteral gold | Penicillamine |
| Intermediate | Methotrexate | Auranofin |
| | | Corticosteroids |
| | | Sulfasalazine |
| Low | | Hydroxychloroquine |

The ability of these drugs to really modify the disease process is controversial. Unlike NSAIDS or Corticosteroids, their onset of action is gradual over weeks to months. In addition, well-defined toxicity's can occur with these drugs, and clinical laboratory monitoring must be judicious. The response rate to the DMARDs is also variable, and patients may gradually lose their positive benefits over time. They exert minimal direct nonspecific anti-inflammatory or analgesic effects, and therefore, NSAIDS must be continued during their administration, except in a few rare cases when true remissions are induced with them. Remittive agents have a wide spectrum of biological effects, but their exact mechanism of action in PA is unknown. Each is associated with considerable toxicity and there is minimal evidence that disease-modifying drugs actually retard the development of bone erosions or facilitate their healing. A brief description of each drug follows.

A. Hydroxychloroquine (Plaquenil)

Hydroxychloroquine is a drug originally developed for the treatment of malaria that has also been used for many years to treat RA and has been somewhat effective among patients with mild to moderate RA. Drug-related adverse effects include gastrointestinal disturbances, skin rash, retinal pigmentary changes and visual impairment, and are more frequently found among older patients. Regular eye examinations once or twice a year because of potential damage to the retina is recommended, and Hydroxychloroquine must be discontinued at the first evidence of visual impairment.

B. Penicillamine (Depen, Cuprimine)

Penicillamine is equally effective in elderly and in younger RA patients. However, its rate of severe toxicity is high, and some adverse effects such as serious skin rashes and taste abnormalities are more common in the older patient. Other adverse effects include nephropathy, bone marrow suppression, gastrointestinal disturbance, autoimmune syndromes, liver toxicity and neuropathy secondary to pyridoxine (vitamin B6) deficiency. Penicillamine is also a slow-acting drug, thus benefit may be achieved only after 3 to 6 months of use. Patients should be monitored with blood counts and urine analyses weekly for the first 4 weeks, then every 4 weeks, with tests of muscle and liver enzymes biannually.

C. Parenteral Gold (Myochrysine, Solganal)

Parenteral gold (intramuscular sodium aurothiomalate or aurothioglucose) has been widely used for 60 years for the treatment of RA. However, gold may lose its effectiveness over time in people who seem to benefit at first. Furthermore, it often takes three to six months to determine whether a person is getting benefits from gold salts and the drug is often discontinued for lack of improvement after the 1000 mg dose is reached.

In some people gold treatment may slow down damage to cartilage and bone. This small group of people with RA experience long-lasting improvement on gold injections, which are given weekly or six months or longer, and can later be tapered to once every three weeks. However, the efficacy of parenteral gold is also hampered by its high rate of toxicity, relative to other remittive agents. Adverse reactions most frequently encountered include skin rashes, oral ulcers, nephropathy and bone marrow suppression. Less common reactions are pneumonitis, enterocolitis and hepatitis. Patients should be monitored with blood counts and urine analyses before each injections, as well as physical examination to look for skin rash and oral ulcers.

D. Auranofin (Ridaura)

Auranofin (oral gold) therapy appears to be less toxic but also less effective than parenteral gold. The spectrum of adverse effects is similar to that of parenteral gold. However, the frequency of gastrointestinal disturbances, especially diarrhea, is higher, while frequency of other toxicity's may be lower. Auranofin's beneficial effects may be achieved only after 2 to 6 months of use. Patients should be monitored with blood counts and urine analyses biweekly initially, then every month.

E. Sulfasalazine (Azulfadine)

Sulfasalazine has been reintroduced recently as a remittive agent in RA. It also appears to have a high toxicity ratio, with adverse effects including skin rash, gastrointestinal disturbances, bone marrow suppression, haemolysis, headaches, hepatotoxicity and pneumonitis. It is contraindicated in patients with a known hypersensitivity to sulfur drugs. There is a paucity of data regarding efficacy profiles. More elderly patients discontinue treatment mainly because of gastrointestinal adverse effects. Patents should be monitored with blood counts, urine analyses and liver function tests biweekly initially, then every month. Sulfasalazine is not yet approved by the FDA for treatment of RA.

F. Azathioprine (Imuran)

Azathioprine is an immunosuppressive drug that has gained widespread use in RA. Data are insufficient to asses its efficacy or toxicity profiles in the general population. It can help RA by suppressing overactivity of the immune system but also can increase susceptibility to certain infections and lower blood counts. Common adverse effects include the aforementioned and increased risk of infections and the development of malignancies. It is recommended that elderly patients be monitored with blood counts and liver function tests biweekly initially, then every month.

G. Methotrexate (Rheumathex)

Since the mid-1980's, methotrexate has become the most prescribed remittive agent for RA in many rheumatology centers. This is due to its higher rate of efficacy and toxicity ratio relative to other remittive agents, its rapid onset of action (mostly within 1 month) and convenient scheduling, with once-weekly dosage of pills or injections. It works more quickly than gold and maintains control of the disease in a larger group population. Unlike gold, methotrexate cannot be taken less frequently after the first 6 to 12 months but instead, must be continued every week.

For the above reasons, methotrexate has proved comparatively effective in controlling joint inflammation in many patients with RA and is often chosen first, especially for individuals with rapidly progressive disease. However, long-term trials have indicated that methotrexate does not induce remission, but rather suppresses symptoms while it is being administered. The other agents are tried when less severe inflammation occurs and if methotrexate has failed or has to be discontinued because of toxicity. However, age is positively related to methotrexate toxicity. Adverse effects include oral ulcers, gastrointestinal symptoms, alopecia, hepatotoxicity, pneumonitis and bone marrow suppression. Transient elevations of liver enzymes occur frequently, but their long term significance is unclear, since they sometimes correlate with histological abnormalities. Fibrosis has been reported in 30 to 52% of patients but there have been fewer reports of cirrhosis. Moreover, sequential liver biopsies in patients continuing methotrexate therapy showed evidence of progression of abnormalities in hepatic architecture. Patients with pretreatment liver abnormalities, alcoholism or lung diseases seem to be at increased risk of developing toxicity in the liver and lung, respectively. Patients should be monitored with blood counts and liver function tests weekly initially, then every month. Kidney functions tests and chest x-ray or pulmonary functions tests should be performed once or twice per year.

H. Alkylating Agents

Alkylating agents cyclophosphamide (Cytoxan) and chlorambucil are very powerful immunosuppressive drugs that are rarely prescribed for the treatment of RA. Despite some proof of efficacy, they can be recommended only for patients with severe, relentless, active RA, not responding to other remittive agents or with serious complications outside the joint such as vasculitis (blood vessel inflammation). This is due to their great risk of frequent and sometimes life-threatening adverse effects, which includes bone marrow suppression, increased susceptibility to infection, and up to a 10-fold increase in the incidence of neoplasia. Other adverse effects are gastrointestinal intolerance, alopecia, pneumonitis and haemorrhagic cystitis. Patients should be monitored with weekly blood counts.

I. Corticosteroids

The role of Corticosteroids (cortisone, prednisone, and other similar medications) in RA is still debated by physicians. In the short run, low dose corticosteroids such as prednisone 5 to 10 mg or cortisone are somewhat effective in some RA patients. However, prolonged administration should be avoided because of long term adverse effects, even with low dosage regimens. These side effects are serious and with respect to cortisone, can include easy bruising, osteoporosis (thinning of the bones), cataracts, weight gain, increased susceptibility to infections, diabetes and high blood pressure. Dosage as low as 5 mg/day of prednisone may suppress the hypothalamic-pituitary-adrenal axis. Other problems include sodium and fluid retention, hypertension, hyperglycaemis, osteoporosis, infections and skin changes.

For any patient taking a corticosteroid on a regular basis, careful attention must be directed to proper calcium, vitamin and hormone regulation. Corticosteroids sometimes are given an injection into one or more joints or other areas of inflammation. Such injections may have harmful side effects on the joints if given more than a few times a year as shown in Table V.

TABLE V

Side Effects of Corticosteroids*

Cataracts (posterior subcapsular)
Glaucoma
Hypertension
Congestive heart failure in predisposed patients
Peptic ulcer disease
Pancreatitis
Cushingoid Appearance (truncal obesity, moon faces)
Hyperglycemia
Secondary adrenal insufficiency
Electrolyte changes (sodium retention, hypokalemia)
Myopathy
Osteoporosis
Aseptic necrosis
Psychosis
Alterations in mood or personality
Pseudotumor cerebri
Thin fragile skin, ecchymoses

*Adapted from Textbook of Rheumatology, W B Saunders Co., 1989, p 852

To date, long term management of RA has required a careful balance of benefit and risk; the estimated relative efficacy and toxicity of remittive agents in patients. Usually therapy begins with the least toxic medications and NSAIDS are prescribed first. If further therapy is needed, hydroxychloroquine, auranofin, or sulfasalazine is added in patients with mild to moderate RA. Methotrexate or parenteral gold may be given in patients with moderately severe disease, or with disease unresponsive to the former remittive agents. Penicillamine, azathioprine and particularly the alkylating agents are reserved for patients with refractory disease. Low dosage prednisone is added for limited periods of time as indicated above, while pulse-therapy with parenteral Corticosteroids can help in the induction of remission of RA. These can be supplemented with intra-articular corticosteroid treatment.

We have now discovered compositions and methods for the treatment of patients suffering from minor to advanced arthritic conditions. The compositions of the present invention effectively replace alternative, state-of-the-art pharmaceutical remedies for persons suffering from rheumatoid arthritis and rheumatoid-related inflammatory diseases.

We have also discovered that the compositions of the present invention can be effectively used in a regimen for delaying of menopause.

Menopause is defined in medial dictionaries as the cessation of menstruation in the human female. Menopause is better described as a transition period marking the closure of reproductive life, usually occurring during mid-life. The average age at last menstrual period in the U.S.A. is 51, though any time between age 40 and 59 falls within the realm of normal. As menopause approaches, the ovaries begin to fail and there is a sudden dip in the female sex hormones, estrogen and progesterone, which causes the cessation of menstruation. About 75 to 80% of women have some symptoms related to the suddenness of estrogen withdrawal.

Throughout most adult lives, the menstrual cycle operates in an expected way, with hormones ebbing and flowing at levels just high enough to keep the system in a comfortable balance. In early puberty, anovulatory cycles (months in which no egg has been produced by the ovary) are signaled by heavier and longer bleeding than normal. The same happens in reverse as menopause approaches. In the months in which ovulation does not take place, periods tend to be heavier and longer. As premenopause (the time when periods are still regular) moves towards the perimenopause (the transition phase between regular periods and no periods at all), monthly events become more unpredictable.

As used herein the definitions of certain terms are as follows.

The word "climacteric" describes the ongoing changes and symptoms of menopause, as it refers to a phase or transition period that my last for 15–20 years, during which ovulation function and hormonal products decline. The climacteric can be divided into 3 stages: pre-, peri- and postmenopause. (Menopause is the point in time signaling the end of premenopause and the beginning of postmenopause.) "Premenopause" refers to the years when the menstrual cycle is regular, or most of the female reproductive life. It also refers to the early years of the climacteric, after the age of 40, when menstrual periods may become irregular and heavy. "Perimenopause" is the stage lasting several years on either side of the last menstrual period. This time marks many physical changes. "Menopause" means the final menstrual period when the female has not had a menstrual period for 12 months. "Postmenopause" overlaps with the end of the perimenopausal stage and extends into the years following the last menstrual period until the end of life.

During the reproductive years, two sources of estrogen production exist. The major source is the secretion of estradiol by granulosa cells of ovarian follicles. The second source involves extraglandular aromatization of plasma androstenedione. The endocrine change associated with the female climacteric are due mainly to the loss of estradiol. Cessation of estradiol secretion is attributed to loss of follicular granulosa cells and to a decreased responsiveness of these cells to follicle-stimulating hormones (FSH). These alterations cause the menstrual cycle initially to shorten and then gradually to lengthen as anovulaton occurs, and eventually to cease completely.

In postmenopausal women, estrogen production occurs almost exclusively by a mechanism known as "peripheral or extraglandular aromatization." This utilizes circulating androstenedione, secreted primarily by the adrenals, and converts it to estrogen in tissue of fat, bone, muscle and brain. Little, if any, estrogen is derived from ovarian or adrenal secretion in menopausal women. In fact, plasma levels of estrogen do not change if the ovaries are removed after menopause. The estrogen production in postmenopausal women is characterized by the extraglandular formation of a biologically weaker estrogen, namely, estrone, rather than by the ovarian secretion of the potent estrogen, namely estradiol.

Although the quantity of testosterone secreted by the menopausal ovary does not change from previous levels, testosterone becomes the principal steroidal hormone secreted by the ovary. The growth of hair on the upper lip and chin of many elderly women may be due to diminished estrogen levels and unopposed action of testosterone in these women. Pubic auxiliary and scalp hair are partially lost, residual hair becomes coarser, mainly due to degeneration of skin and loss of skin appendages rather than to hormonal alterations.

Common symptoms associated with menopause are briefly described hereunder.

There exists a wide range of symptoms that commonly affect women during menopause. Despite the documented occurrence of all of the ailments, most medical texts recognize three major physical ailments, which are menstrual irregularity, hot flashes, and dry vagina (a.k.a. "genitourinary distress"). Osteoporosis is occasionally listed as a symptom, but it is really a condition beginning long before menopause, but which may become critical during the menopausal years. Psychological ailments (anxiety, depression and panic attacks) are viewed and handled differently depending on the source of the expert consulted.

Symptoms of menopause may be both long and short term. Short term symptoms include hot flashes, night sweats, loss of libido. Long term symptoms include the thinning and drying out of the vaginal and genital skin and urinary troubles, which may all become permanent. Standard sings of menopause are:

1) Menstrual irregularity, or a fluctuation in the menstrual cycle. Periods may continue to arrive in a timely manner, but there are usually minor changes. For example, the period that lasted 3 or 4 days may last for 2 or 6; the flow might be much grater than typical or the color of the flow may change. All of this is normal, as is the increasing tendency to skip a period.

2) Hot flashes and night sweats, are another very common physical symptom. A hot flash is the sudden sensation of heat. When experienced at night they are called night sweats. Cold chills are not uncommon either. A hot flash is described as a sudden onset of warmth in the face and neck that progresses to the chest, making the neck and face red. It is estimated that 75 to 85% of American women experience hot flashes, marked by a rise in body temperature and a feeling of unbearable heat. The veins of the hands may tingle and swell. Perspiration may bead at the hairline, between the breasts and down the back. Hot flashes can last from one minute to an hour, but they usually last 2 to 3 minutes and are frequently associated with dizziness, nausea, headaches and palpitations. They tend to appear during the time when menstrual periods are erratic and to peak during the year of the last menstrual period. They seem to occur most often just before rising and just before bed.

The combination of a rise in skin temperature, peripheral vasodilation, a transient increase in heart rate and changes in skin impedance is also known as vasomotor instability. 80% of women who experience hot flashes have symptoms for more than 1 year, but less than 25% have symptoms for more than 5 years. It is said than not all post menopausal women experience vasomotor symptoms, perhaps because of alterations in metabolism of catecholamine or catecholestrogen within the brain or because of extraglandular formation of estrone was sufficient in these women to suppress the symptoms. Thus, it appears that hot flashes are triggered by "estrogen withdrawal" rather than by a lack of estrogen. The exact mechanism(s) responsible for the vasomotor flush is unknown, although the hypothalamus is the likely site or origin of vasomotor flush.

3) Dry vagina and urinary distress. With menopause's onset, the tissue of the urethra and vagina tend to thin out and become more fragile. The vagina may also become shorter and both urethra and vagina become more vulnerable to inflammation and infection. This atrophy of the epithelium ultimately leads to symptoms of irritation, burning, pruritis and vaginal bleeding at times. The loss of the vaginal epithelium correlates with the extent of estrogen deprivation and tends to worsen with time. This condition is likely to occur a few years after menopause and may mean that a women's own lubrication is inadequate for pleasurable penile penetration. The reduction of lubrication during intercourse is due mainly to a decrease in vaginal fluids, blood flow and glycogen production.

More specifically, during reproductive years the vaginal pH is between 4.0 and 5.5 due to the production of glycogen-rich superficial cells. As ovarian function begins to wane, this maturational process is lost and the vaginal pH increases to a range between 6.0 and 8.0. These changes lead to a higher incidence of vaginitis.

Even when vaginal or urinary problems are relatively minor, many woman complain of frequent urination and a tendency to leak when coughing, sneezing or during orgasm. This is known as stress incontinence. Urge incontinence is diagnosed when urine is dribbled on the way to the toilet. Both conditions are treatable.

4) Osteoporosis, or "porous bone", is a condition that results from excess loss of bone tissue. The onset is usually painless, with no advance warning, except for occasional lower back pain as crush fractures happen. Because the pain eases after a few days, few women suspect that a vertebra may have collapsed. The first awareness of osteoporosis for most women is a fracture of some sort.

Normally the amount of new bone formed is equal to or greater than that resorbed. In osteoporosis, bone resorption is greater than bone formation. Maximum bone density is reached between the ages of 25 and 36 years. By the age of 45 to 50, the rate of bone resorption is greater in women than in men and more prevalent in Caucasians than in blacks. After our mid-30's, we begin to lose bone slowly at first and then more quickly in our late 40's and early 50's. Once menopause is past, bone loss slows down again.

Although we recognize an association between estrogen deprivation and progressive loss of bone mass, the role of estrogen in the pathogenesis of post menopausal osteoporosis is still not entirely clear. The balance between the rate of bone formation and resorption is complex and involves a sensitive relationship between dietary calcium intake and absorption, serum concentrations of calcium and phosphorus, and other issues. There are no specific estrogen receptors in bone, and estrogen per se does not stimulate osteoblastic activity. However, estrogen therapy does reduce urinary calcium excretion, (it is presumed) by increasing calcium absorption in the renal tubules.

Thus, while considerable evidence has accrued which lends credibility to the existence of a causal relationship between estrogen deprivation and osteoporosis, the issue of whether estrogen deprivation is the primary cause of osteoporosis has not been resolved. Generally, in estrogen deficient premenopausal women, bone loss is accelerated but corresponds more to the time of ovarian loss rather than to chronological age. Furthermore, women who are menstruating after age 50 have a slower rate of bone loss than do menopausal women of similar age.

5) Psychiatric Symptoms. The female climacteric may be quite stressful. Many menopausal women experience nervousness (easy excitability, mental and physical unrest), irritability (uncontrollable crying, frequent rage or anger), anxiety (feelings of apprehension, uncertainty, fear and loss of self-image), and depression (inability to make decisions, apathy, psychomotor retardation, loss of libido or loss of emotional reaction). Most scientists feel that depression is not hormone-dependent. And the diagnosis of "involutional melancholia" which was previously used to describe menopausal depression, has been deleted from the list of acceptable diagnostic codes.

Additionally, the menopausal headache may have many causes which do not relate to estrogen deprivation, such as the hormonal therapy itself. Estrogen therapy alters REM ("rapid eye movement") sleep and the number of waking episodes associated with hot flashes in menopausal women.

We have come to learn the affect that our composition has on the climacteric only coincidentally after doing research related to the rheumotoid-based diseases. The compositions seems to extend the premenopause period, delaying menopause and therefore, postmenopause. The exact mechanism (s) responsible for this is unknown, although we suspect that certain component(s) of the composition stimulate the adrenal glands, counteracting the decline in estrogen production and encouraging the production of yet another hormone, cortisone.

With respect to the affect that the compositions have on rheumatoid-based diseases, we do not know how the inflammation triggering the onset of these diseases is controlled or abated, although this is the affect the compositions have.

Acute inflammatory dermatoses and chronic inflammatory dermatoses are usually mediated by local or systemic immunological factors, although their causes generally remain a mystery. Thousands of specific inflammatory dermatoses exist. Some have both acute and chronic stages, others are most characteristic in early or late stages. In general, acute lesions last form days to weeks and are characterized by inflammation, edema and sometimes, epidermal, vascular or subcutaneous injury. Chronic lesions, on the other hand, persist for months to years and often show significant components of altered epidermal growth (atrophy or hyperplasia) or dermal fibrosis.

Eczema falls into the category of acute inflammatory dermatoses. It is an umbrella clinical term embracing a number of pathogenetically different conditions. Al conditions are characterized by red, papoluvesicular, oozing and crusted lesions early on that with persistence eventuate into raised, scaling plaques. It has an acute phase which can become a chronic eruption if untreated. With time, persistent lesions become less "wet" (fail to ooze or form vesicles) and become progressively scaly.

Urticaria or hives refers to a common disorder of the skin characterized by localized mast cell degranulation and resultant dermal microvascular hypermeability falls into the category of acute inflammatory dermatoses. Individual lesions develop and fade usually within 24 hours, and episodes may last for days or persist for months. Persistent urticaria may simply be the result of inability to eliminate the causative antigen or may herald underlying diseases. Lesions may vary from small pruritic papules to large endematous plaques.

Erythema Multiforme falls into the category of acute inflammatory dermatoses. It appears to be a hypersensitivity response to certain infections and drugs. Patients have array of lesions including macules, papules, vesicles and bullae, as well as the characteristic target lesion consisting of a red macule or papule with a pale, vesicular or eroded center.

Psoriasis falls into the category of chronic inflammatory dermatoses. It is sometimes associated with arthritis, myopathy, enteropathy, spondylitic heart disease and AIDS. Psoriatic arthritis may be mild or produce deformities resembling the joint changes seen in rheumatoid arthritis. Most frequently affects elbows, knees, scalp, lumbosacral areas, and glans penis. Most typical lesion is well-demarcated, pink and salmon-colored plaque covered by loosely adherent scales that are characteristically silver-white in color. Psoriasis can be the cause of total body erythema and scaling known as erythroderma.

Lichen Planus falls into the category of chronic inflammatory dermatoses. Pruritic, purple, polygonal papules are signs of this skin disorder. It is self-limiting and generally resolves spontaneously one to two years after onset, often leaving zones of post-inflammatory hyperpigmentation. Oral lesions may persist for years. Lesions are itchy, flat-topped papules that may coalesce locally to form plaques often highlighted by white dots or lines called Wickman's striae. Multiple lesions are characteristic and symmetrically distributed, particularly on the extremities, often about the wrists and elbows.

Gingivitis is the most common form of periodontal disease starting as inflammation of the marginal gingiva which is painless, although the gingiva may bleed on brushing. The disease spreads to involve the periodontal ligament and alveolar bone. As the alveolar bone is slowly resorbed, there is loss of periodontal ligament attachment between tooth and bone. The soft tissue separates from the tooth surface, causing "pocket" formation with bleeding on probing and during chewing. Acute inflammation may become superimposed on this chronic process, with the production of pus and formation of a periodontal abscess. Ultimately, extreme bone loss, tooth mobility, and recurrent abscess formation leads to tooth exfoliation or may mandate tooth extraction. It is infection associated with the accumulation of bacterial plaque which may become mineralized ("calculus") and which can be prevented by appropriate oral hygiene measures including tooth brushing, flossing, antibacterial mouth rinses, and the removal of impacted food debris.

SUMMARY OF THE INVENTION

I. Topical Composition and Method of Treatment of Rheumatoid-Based Diseases a) For the treatment of rheumatoid-based diseases the composition of the present invention comprises:

300 to 1500 grams, and preferably 700 to 1000 grams of finely divided powder of safflower seeds (carthamust inctorius l) admixed into 6 to 7 gallons of warm water.

The method of treatment comprises:

bathing the patient in the composition for about 0.5 to 1.5 hours;

towel drying the patient;

allowing the residual composition to remain on the patient for 24 hours; and repeating the treatment at least twice a week for 6 to 10 weeks or longer.

(b) In another embodiment the composition of the present invention comprises:

150 to 1000 grams, and preferably 300 to 800 grams of an extract of safflower seeds admixed into 6 to 7 gallons of warm water.

The method of treatment comprises:

bathing the patient in the composition for about 0.5 to about 1.5 hrs;

towel drying the patient;

allowing the residual composition to remain on the patient for 24 hours; and repeating the treatment at least twice a week for 6 to 10 weeks or longer.

(c) Alternatively, the treatment of patients having rheumatoid-based diseases comprises massaging an extract of safflower seeds onto the affected joint areas of the patient for about 5 to 20 minutes, preferably for 10 to 15 minutes.

II. Compositions and Method of Treatment for Menopause

For the treatment of menopause a combination of topical and oral formulations are used. The topical treatment is as above-described in I(a) and I(b), except that the duration of treatment is extended for as long as necessary.

The oral component of the treatment comprises:

ingesting an oral formulation containing of from about 25 to 30 grams of an extract of safflower, or 30 to 100 grams of finely divided safflower seed twice a week as long as necessary.

While the compositions and treatments described in I and II above defines the specifics as best determined at present and supported by testing on human patients, it is to be understood that a broader aspect of the invention encompasses treatment of rheumatoid-based diseases and menopause by using a "therapeutically effective amount" of said compositions. "Therapeutically effective amount" refers to the amount of an active agent sufficient to induce a desired biological result. That result is the alleviation of the signs, symptoms, or causes of the diseases or conditions described under Reported Developments.

III. Method of Treatment of:

Inflammatory Diseases, such as Eczema, Urticaria, Psoriasis, Erythema Multiforme and Lichen Planus, Inflammation of the Gums, and Chronic Localized Bodily Pain Derived From Acute Injury The treatment for the relief of inflammation and or pain associated with inflammatory dermatoses such as eczema, urticaria, psoriasis, erythema multiforme and lichen planus, gingivitis, and acute injury in a mammal comprises: topically administering to said mammal in need of such treatment a therapeutically effective amount of a finely divided powder of safflower seed having a particle size of 100 microns or less or its extract sufficient to induce alleviation of signs, symptoms or causes of inflammation or pain in a pharmaceutically acceptable carrier. The "Therapeutically effective amount" refers to the amount of an active agent sufficient to induce a desired biological result. That result is the alleviation of the signs, symptoms, or causes of the diseases or conditions described under Reported Developments. "Finely divided powder" denotes an average particle size of 100 microns or less.

DETAILED DESCRIPTION OF THE INVENTION

Certain compositions of the present invention are oral while others are topical, and accordingly, their method of administration are either oral or topical or a combination of oral and topical.

For oral compositions it is contemplated that any system which affords ingestion via the gastrointestinal tract can be used, such as powders, pellets, tablets, suspensions, gels, candy bars, chewing gums, syrups and beverages.

For topical compositions it is contemplated that any system which provides delivery of the active ingredients to an appropriate site of the body can be used, such as dried and comminuted safflower seeds contained in a water-penetrable bag or container to be used in water, ointments, creams, lotions, solutions, dressings and patches, slow-release preparations and film-forming preparations. The topical compositions may contain certain pharmaceutical and therapeutical agents that can be included in the compositions either singularly or in combination. Such agents include: anti-inflammatory analgesics such as salicylic acid, salicylate esters and salts, acetylsalicylic acid, acetaminophen, phenylbutazone, indomethacin, fenoprofen, ibuprofen and ketoprofen; local anesthetics such as benzocaine, lidocaine and bupivacaine; antibacterial agents such as sulfanilamide, sulfadiazine, sulfisoxazole and trimethoprim; antiseptic agents such as ethanol, isopropyl alcohol, chlorhexidine, hexachlorophene and benzoyl peroxide; anti-inflammatory corticosteroids such as progesterone, hydrocortisone, prednisone, triamcinolone and dexamethasone; and vasodilators such as niacin, nicotinate esters, diltiazem and indomethacin.

We have found that one of the most effective methodology of treatment is by bathing in water in which finely divided particles of raw safflower seeds are dispersed. In this methodology the seeds of the safflower are removed and comminuted to fine particle size, preferably 100 micron or less, packaged in a porous packet and immersed in warm bath water. The patient, while in the bath water then rubs the content aggressively until the content dissolves or at least homogeneously dispersed in the water. The patient remains in the bath for 30 to 90 minutes while subjecting the inflamed rheumatoid area of the body to the therapeutic bath. We have found that for best results the ratio of ground safflower seed to the volume of water is about 300 to 1500 grams of powder to 6 to 7 gallons of water.

Alternatively, the safflower seeds may be dried to eliminate moisture that might be present in raw safflower seeds, followed by comminution to the desired particle size.

The porous packet is packaged in a moisture/gas impermeable package to prevent degradation of the content.

It is to be noted that the present invention utilizes seeds of safflower or extract of safflower seeds and not the commercially available oil of safflower. While safflower oil has been found to be beneficial as a component of dietary supplements and as an important food source, it appears that certain trace amounts of ingredients are lacing in such commercially available oils without which the beneficial effect is not obtained as described by the present invention.

The extract of safflower seeds are obtained by methods known in the art for extracting ingredients from naturally occurring sources and includes:

the shelled safflower seeds are crushed and comminuted to a small particle size of 100 micron or less;

mixing the fine particle-size powder with an organic solvent, such as acetone, methylethylketone, diethylketone, methanol or ethanol;

allowing the mixture to stand at a low temperature, such as at room temperature, to dissolve soluble compounds from the powder;

separating the extract from the unsolvated material by filtration; and evaporating or distilling the solvent to obtain the desired extract of the safflower powder.

Alternatively, the finely divided safflower powder can be mixed with hot methanol or hot ethanol to accelerate the dissolution process.

Both the extract or the finely comminuted safflower powder can be made into pharmaceutical compositions as illustrated hereunder.

While it is possible to administer the finely divided safflower seed or its extract alone, and their topical administration via bathing is preferred, it is practical to provide various forms of administration for the convenience of the patients. These forms include solid, semi-liquid, and liquid dosage forms, such as tablets, pills, powders, solutions and suspensions.

Topical Formulations

Topical formulations can be prepared by combining the finely divided safflower seed or its extract with conventional pharmaceutical carriers or diluents used in topical dry, liquid and cream formulations. Ointments and creams may be formulated with an aqueous or oil base with the addition of suitable thickening or gelling agents.

Lotions may be formulated with an aqueous or oily base, and will include stabilizing agents, emulsifying agents, dispersing agents, suspending agents, thickening agents, coloring agents and the like.

Powders may be formulated with the aid of any suitable powder base, such as talc, lactose, starch and the like.

The ointments, pastes, creams and gels may contain excipients, such as paraffins, starch, tragacanth, cellulose derivatives, polyethylene glycols, silicones, talc and zinc oxide.

The topical pharmaceutical formulations may include one or more preservatives or bacteriostatic agents, such as methyl hydroxybenzoate, propyl hydroxybenzoate and benzalkonium chloride.

Another preferred form for topical delivery of the finely divided powder of safflower seed or its extract is a hot compress comprising:

a woven or non-woven fibrous wrap impregnated with said finely divided safflower seed or its extract, dried and packaged for use. Prior to treatment the impregnated fibrous wrap is immersed in warm water to at least partially solubilize the active component and is wrapped around the rheumatoid-based disease infected area.

Another preferred form of topical delivery is film-forming materials loaded with the finely divided powder of safflower seed or its extract. Such film-forming materials are disclosed in U.S. Pat. No. 4,623,539 and is incorporated herein by reference.

The film-forming polymers include certain anionic, cationic and neutral polymers.

A) Anionic polymers suitable as film-forming materials are represented by the generalized formula:

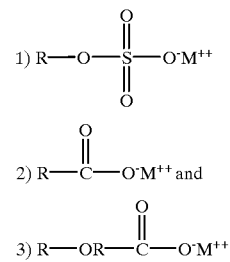

wherein
R is a polymeric chain or residue;

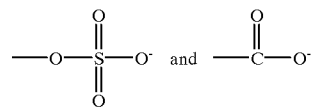

are anionic ligands; and

M is a divalent cation of $Mg^{++}$, $Ca^{++}$, $Zn^{++}$ or $Ba^{++}$.

Specific anionic polymers include:
sulfated polysaccharides;
carboxylated polysaccharides;
cellulose derivatives; and
sulfated, sulfonated or carboxylated synthetic polymers.

Sulfated polysaccharides include sugars, cellulose, starch and glycogen.

Carboxylated polysaccharides include pectin, algin and karaya gum.

Cellulose derivatives include sodium ethylcellulose sulfate, sodium cellulose acetate sulfate and sodium carboxymethyl cellulose.

B) Cationic polymers suitable for film-forming materials are represented by the following formulas:

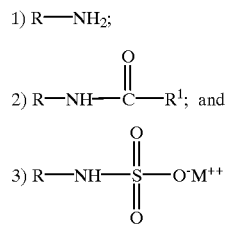

wherein
R is a sugar residue;
$R^1$ is $CH_3$ or $C_2H_5$, and
$M^{++}$ is $Mg^{++}$, $Ca^{++}$, $Zn^{++}$ or $Ba^{++}$.

Examples of specific cationic polymers include chondrotoin sulfate, dermatan sulfate, keratosulfate, hyaluronic acid, heparin and chitin.

C) Neutral polymers suitable as film-forming materials include:

polysaccharides, such as fructans, mannans, galactomannans, glucomannans, dextran and starch amylose;

cellulose derivatives, such as methylcellulose, hydroxyethylcellulose, ethylhydroxyethyl cellulose and hydroxypropyl cellulose; and synthetic polymers, such as polyvinylpyrrolidone, polyvinyl alcohol and the ethylene oxide polymers.

These polymeric materials are capable of forming a film in the pH environment of 5.5 to 8.5 and contain atoms with polarizable electrons thereon such atoms being oxygen, nitrogen and sulfur. These atoms in the polymeric materials in combination with the divalent cations of $Ca^{++}$, $Mg^{++}$, $Zn^{++}$ or $Ba^{++}$ provides for the formation of a film on a solid surface, such as the skin of the patient. The ratio of the oxygen, nitrogen or sulfur atoms to the divalent cations of $Ca^{++}$, $Mg^{++}$, $Zn^{++}$ or $Ba^{++}$ is preferably in the range of 7.7 to 1.

The film-forming materials described above are mixed with the finely divided powder of safflower seed or its extract and suspended in an aqueous/alcoholic vehicle, such as ethanol, or incorporated into a lotion or cream base. The ratio of the film-forming material to the active ingredient is about 1 to 10 and preferably about 3 to 5.

Upon application, the formulation is deposited on the desired area and allowed to form a film which, by the presence of water in the skin environment, will allow slow delivery of the active agent onto the area being treated.

Oral Formulations

Formulations in the form of tablets, capsules, suspensions, solutions and the like well-known in the pharmaceutical art are used for delivery of the finely divided powder of safflower seed or its extract to the patient.

Our compositions have been clinically tested on volunteers having rheumatoid-based diseases suffering from minor to advanced arthritic and/or other rheumatoid-based symptoms and conditions. The results confirm that the application of our compositions is a breakthrough in healing patients afflicted with these diseases. It is expected that our compositions will replace many alternative pharmaceutical and surgical remedies for the large majority of persons suffering from arthritis and rheumatoid-based diseases because (1) it cures the patient by reducing the inflammation that triggers the onset of many rheumatic diseases, eliminating symptoms and preventing progressive damage to articular structures; (2) it is non-toxic with no side effects; (3) treatment is noninvasive and simple; and (4) if recurrence of certain disease symptoms does take place, usually one to two follow-up treatment(s) sufficiently achieves remission.

Clinical testing of our compositions have included laboratory testing described hereunder.

Laboratory testing in RA is important and must be carefully coupled wit the clinical findings. In the effort to facilitate understanding of why certain blood tests are performed, one must learn about the immune system, which in a nutshell is the body's natural defense against foreign invaders such as bacteria or viruses. Many rheumatic diseases are known as autoimmune diseases and can be traced to a defect in one's immune system. The immune system fights its own body cells because it interprets them as invaders. When an invader such as a virus enters the body, the virus creates an antigen. The body's immune system fights the antigen by creating an antibody. When the immune system incorrectly decides the body itself is an invader, it creates autoantibodies that attack the body itself. The results of this process include inflammation of the joints, muscles, internal organs, skin, blood vessels, eyes or mucous membranes. Immunological blood tests, such as rheumatoid factor, antinuclear antibody, and Human Leukocyte Antigen tissue typing, are often used to diagnose an autoimmune disease.

(1) Rheumatoid Factor

The hallmark of RA is the presence of rheumatoid factors (hereinafter, "RF"), which are anti-human immunoglobulins (hereinafter "IgMs"). The rheumatoid factor test measures whether a certain amount of abnormal antibody called RF is in the blood. "Classic" RF is an IgM antibody directed against IgG and is detected in 80% of patients with RA. However, this test is not specific for RA and may be found at times in the other connective-tissue diseases, in chronic inflammatory states, and occasionally in normal individuals. Its use as a screening test in all patients with arthritis should therefore be avoided. In the first three months of RA when the diagnosis is often difficult, RF is present only in one quarter of cases. By 1 year, almost all who will be RF positive have become so. Why 20% of patients with RA do not develop IgM RF is not clear. Patients with positive RN, especially in high titer, tend to have more severe articular diseases, rheumatoid nodules, and systemic manifestations.

(2) Antinuclear Antibody Tests.

antinuclear antibody (hereinafter "ANA") tests detect a group of autoantibodies that are found in most people afflicted with lupus and in a few people with RA. The most important ANA is called anti-DNA, which reacts with DNA (the chemical material in the nucleus of a cell that makes up the genetic component).

(3) Human Leukocyte Antigen Tissue Typing

These tests detect whether certain genetic markers or traits are present in the blood. For example, B-27 is the name of a genetic marker that is almost always present in people with ankylosing spodylitis (a disease involving inflammation of the sacroiliac joint and spine) and Reiter's syndrome (a disease involving inflammation of the urethra, eyes and joints).

(4) X-Rays/Radiographs

Radiological findings in the joints in RA are related to the synovial membrane inflammation. Early in the course of the disease roentgenograms may be normal. With time, the bones become demineralized with osteoporosis, especially in the regions adjacent to the joints (juxta-articular osteoporosis). In addition, the proliferative synovium, known as the pannus, can erode into the articular cartilage and bone causing considerable damage. Increased synovial fluid production results in joint swelling that when coupled with the extension of the inflammation into the peri-articular tissues results in laxity of the surrounding ligaments and adjacent tendons. Significant deformity of joints can develop, especially in the hands and feet as a result of concomitant mechanical stresses on the involved joints. Common clinical findings include swan neck, boutonniere, and ulnar deviations deformities of the hands and metatarsophalangeal subluxation of the feet. Other joints, including the hips, knees, shoulders, elbows and ankles, may have severe cartilage and bone changes. The upper cervical spine may be involved with atlantoaxial subluxation, which may cause spinal cord impingement by the odontoid process of the C2 vertebra. Intermittent radiographic evaluation of the neck may be warranted to detect slippage prior to this catastrophic occurrence.

(5) Joint Fluid Tests

Inserting a needle into a joint and removing or aspirating fluid form it can provide the doctor with valuable information. Usually this procedure is conducted with local anesthetics. An examination of the fluid may reveal what is causing the inflammation, such as uric acid crystals, a sure sign of gout, or bacteria, a sign of infection. In addition, joint aspiration can sometimes relieve the pain of a badly swollen joint by draining of some of the inflamed synovial fluid (the fluid that surrounds a joint, providing for smooth movement).

In testing a composition of the present invention it was unexpectedly discovered that the composition is also effective in healing certain soft tissue rheumatic syndromes (hereinafter sometimes referred to a "STRS"), in addition to RA. These are syndromes that affect the tissues and structures that surround a joint and produce pain, swelling or inflammation, including tendons, ligaments, bursae and muscles. Since these structures are near the joint, pain in these areas may easily be mistaken for arthritis, However, arthritis refers to inflammation in the joint itself, not the structures around the joint.

One or more of the following factors can cause STRSs: overuse or injury to the joint areas form repeated activity, incorrect posture or poor conditioning before exercise, an abnormal or poorly positioned joint or bone that stresses soft tissue structures, an infection, in association with other diseases or conditions like RA, often an unknown cause.

Pain is the major complain in people with an STRS. Pain usually starts suddenly. Since the structures involved are located near the joint, movements of that joint can be extremely painful and limited. Some conditions are associated with redness, warmth and swelling.

The two most common conditions favorably affected by our composition are tendinitis and carpal tunnel syndrome. Tendinitis is inflammation or irritation of the tendon, which is a thick cord that attaches muscle to bone. Tendons convey the power generated form muscles to move a bone. Carpal tunnel syndrome [hereinafter sometimes referred to as "CTS"] is a condition that causes pain, tingling, numbness and/or weakness in the fingers and thumb due to pressure on the median nerve. This nerve carries signals between the hand and brain. In the wrist, the median nerve and several tendons that allow the fingers and thumb to bend pass through the carpal tunnel (a tunnel created by the wrist bone and other tissue). When swelling or inflammation occurs around the tendons and nerve, pressure is increased within the carpal tunnel which affects median nerve function, causing the symptoms of CTS.

With respect to STRSs, causes often include arthritis-related diseases, such as RA. Our composition has been highly effective in the treatment of STRS patients with histories of RA, which comes as no surprise considering the overwhelmingly positive clinical results of our composition's application on RA patients.

A composition according to the present invention was tested on patients suffering primarily form rheumatoid arthritis, as well as osteoarthritis, carpal tunnel syndrome and tendinitis. The method of testing comprised:

The patient was placed in a private whirlpool spa where 700 grams of an extract of safflower powder was diluted in 6 to 7 gallons of warm water. The patient remained in the spa for 1.5 hrs after which the patient was towel-dried and instructed not to shower for 24 hrs. In some instances, the extract was massaged onto the affected joint area for 15 minutes.

The following is a list of case studies representing patients treated with the composition.

Arthritis grading scale used is shown in Table VI.

TABLE VI

Arthritis Grading Scale

| Grade | Descriptive Evaluation |
|---|---|
| 0 | no disease |
| 1 | documented disease that is asymptomatic |
| 2 | mild pain that is relieved by nonopiate analgesics |
| 3 | severe pain that is not relieved by analgesics |
| 4 | disabling pain that interferes with the activities of daily living |

Table VII shows the Synopsis Chart.

TABLE VII

Synopsis Chart

| Case | Patient | Age | Sex | Duration of Disease | Pre-Tx* Grade | Post-Tx* Grade | Diagnosis |
|---|---|---|---|---|---|---|---|
| 1 | MK | 84 | F | 35 Years | 4 | 1 | RA |
| 2 | PY | 56 | F | 26 years | 4 | 1 | RA/OA |
| 3 | TJ | 65 | F | 12 years | 3 | 1 | RA |
| 4 | HK | 44 | F | 4 years | 4 | 1 | RA/CTS |
| 5 | SL | 48 | F | 15 years | 4 | 1 | RA |
| 6 | AOP | 58 | F | 29 years | 4 | 2 | CTS |
| 7 | JMC | 70 | F | 15 years | 4 | 1 | OA |
| 8 | FRB | 65 | M | 6 years | 4/3 | 1 | RA |
| 9 | TK | 75 | F | 3 years | 3 | 1 | RA |
| 10 | MRM | 89 | F | 13 years | 4/3 | 2/1 | CTS |
| 11 | WW | 55 | M | 20 years | 4 | 1 | RA |
| 12 | AHP | 70 | F | 8 years | 4 | 2 | OA |
| 13 | MBG | 85 | F | 16 years | 4 | 1 | RA |
| 14 | ACG | 76 | M | 25 years | 4 | 2 | RA/CTS |
| 15 | NS | 67 | F | 20 years | 4 | 2 | RA/CTS |
| 16 | RP | 67 | M | 7 years | 3 | n/a | RA/CTS |
| 17 | CJK | 38 | F | 4 years | 3 | n/a | RA/CTS |
| 18 | DGB | 64 | F | 6 years | 4 | 4 | OA |

*Tx is an abbreviation for treatment

Clinical summary follows.

Case #1:

MK is an 84 year old female ("F") with a history of ("ho") RA for 35 years ("yrs"); previous medical history ("PMH") is also significant for congestive heart failure ("CHF"), myocardial infarction ("MI") and diabetes; MK on multiple medications, i.e., coumadin, micronase, furosamide and lanoxin; pain increased ("++") over the course of 20 yrs to the point where it interfered with ("w/") activities of daily living ("ADL"); Tx was undertaken for 3 months ("mths") after which mobility was regained. Now w/follow-up ("f/u") of 2 yrs, MK remains asymptomatic.

Case #2:

PY is a 56 year old F w/ h/o RA and OA for 26 yrs; PMH is also significant for cerebrovascular accident ("CVA"), herniated nucleus pulposis in the lumbar region ("HNPL"), and erythmia; PY has taken Naproxen, other NSAIDS and steroidal drugs to no avail; pain ++ over the course of 18 yrs, to the point of interference w/ ADL; Tx was undertaken for 2 mths w/ f/u Tx after 6 mths; f/u of 3 yrs reveals no recurrence of inflammation or pain.

Case #3:

TJ is a 65 F w/ h/o RA for 12 yrs; PMH is also significant for CVA; TJ has tried NSAIDS, DMARDS and Alkylating Agent s("AAs"); pain ++ for past 12 yrs, particularly when in between drugs; interference w/ ADL, Tx undertaken for 1 mth; f/u reveals complete remission for past 1 yr.

Case #4:

HK is a 44 F w/ h/o RA and Carpal Tunnel Syndrome ("CTS") for 4 yrs; was recommended surgery to relieve pressure on median nerve; pain ++ for 1 yr w/ interference w/ ADL; Tx undertaken for 3 weeks ("wks"); f/u reveals complete remission w/ no reports of stiffness, pressure or numbness for past 3 yrs.

Case #5:

SL is a 48 F F w/ h/o RA for 15 yrs systematically affecting most of her joints; PMH is also significant for high blood pressure and CTS surgery; SL has tried methotrexate, auranofin, lederfen and corticosteroids; pain ++ for 15 yrs w/ interference w/ADL; Tx undertaken for 2 wks; f/u reveals her asymptomatic for past 5 mths.

Case #6:

AOP is a 58 F w/ h/o RA CTS on both wrists for 29 yrs; PMH includes CTS surgery for right median nerve, diabetes and high blood pressure, AOP has tried NSAIDS; Tx is being currently administered with 2 Txs undertaken w/in a 2 wk period; f/u reveals a decline in pain by 50%.

Case #7:

JMC is a 70 F w/ h/o OA in both knees for 15 yrs; PMH includes MI, four heart attacks, diabetes and obesity; JMC on Procardia, micronase, Lasix and Potassium; has tried NSAIDs w/++ of pain; 7 Txs undertaken for 2 mths; f/u asymptomatic for past 4 mths.

Case #8:

FRB is a 65 year old male ("M") w/ h/o RA affecting joints of the hand, knee, ankle, feet and neck for 6 yrs; PMH is also significant for high blood pressure and anticoagulants; has tried various Txs including cortisone and NSAIDS; 6 Txs were undertaken for 5 wks; f/u asymptomatic for past 2 mths.

Case #9:

TK is a 75 F w/ h/o RA for 3 yrs affecting her knees, hips, spine and shoulders; has tried NSAIDs, DMARDs and a combination of Cortisone w/ Relafin w/pain ++; 3 Txs undertaken for 2 wks; f/u asymptomatic for past 2.5 mths.

Case #10:

MEM is a 89 F w/ h/o CTS affecting both wrists for 13 yrs; PMH includes glaucoma, diabetes and a kidney operation; MEM has tried NSAIDS; 3 Txs being currently administered has reduced her pain by 60%.

Case #11:

WW is a 55 M w/ h/o RA for 20 yrs affecting fingers of the hands,; has tried methotrexate, auranofin and corticosteroids; pain ++ for 15 yrs; interference w/ ADL; Tx undertaken for 3 wks; f/u asymptomatic for past 9 mths.

Case #12:

AHP is a 70 F w/ h/o OA for 8 years affecting both knees; PMH is also significant for high blood pressure and obesity; has tried NSAIDS after pain ++ over 3 years; 6 Txs undertaken during 5 wks which has diminished pain by 40% to date.

Case #13:

MBG is a 85 F w/ h/o RA affecting knees and hips for 16 yrs with intense progression over the past 6 mths; PMH includes high blood pressure, mitigated by Procardia; has tried NSAIDS but pain ++; currently 3 Tx administered that reduced pain by 50%.

Case #14:

AGC is a 76 M w/ h/o RA affecting the neck, shoulders, elbows, wrists, hand joints, hips, knees and lower back; PMH is also significant for MI and bypass surgery, CTS surgery, lyme disease and hernia; currently on anticoagulants, Quinidine, nitroglycerin, Procardia and NSAIDS for the RA but pain ++; 3 Txs have reduced the neck and shoulder pain by 20%.

Case #15:

NS is a 67 F w/ h/o RA affecting the neck and shoulders for 20 yrs and CTS affecting the wrists and fingers for 6 mths; PMH includes cardiac arrhythmia, high blood pressure and bursitis; currently taking Xantex, Digitalis, Lasix and Norwak; NSAIDS did not help the pain; 4 Txs reduces the pain by 70% over 5 wks.

Case #16:

RP is a 67 M w/ h/o RA affecting knees and CTS progressively intensifying during past 7 yrs; currently taking NSAIDs; RP is under Tx, with some pain relief evident after one Tx.

Case #17:

CJK is a 38 F w/ h/o CTS and pinched nerve, suspicion of RA due to symptoms affecting jaw, shoulders, wrists, thumbs, and joints, knees, ankles, feet joints and upper back; currently under Tx, with progress reported after one Tx.

Case #18:

DGB is a 64 F w/ h/o OA of knees, severely debilitating her ability to walk; also obesity; was taking NSAIDS; DGB is our only patient who did not improve after 5 Txs.

The composition arrests the development of the rheumatoid-based diseases, its nontoxic nature resolves any concerns about side effects. As such, it represents a breakthrough in healing patients afflicted with RA and RA-induced STRS', because it is the first non-toxic treatment with no side effects that reduces inflammation triggering the onset of these diseases.

Menopause patients were also treated by the methods and compositions of the present invention.

Twenty patients were treated between the ages of 42 and 58. Each patient had experienced virtually all of the symptoms associated with menopause, such as hot flashes, headaches, weight gain, insomnia, decreased libido, depression, lethargy and joint pain. Each patient was "in menopause", having had her last period between 7 months and 4 years prior to the treatment. Ten patients were treated only topically using the method described in connection with treating patients with rheumatoid-based diseases. The other ten patients were treated, in addition to the topical treatment, with an oral formulation. The oral formulation, a "tea" containing 25 to 30 grams of the finely divided powder of safflower seed, was consumed twice a week for four weeks.

The result, based on evaluation of input from each patient, was:

patients who were treated topically exclusively, experienced normal menstrual period within 4 weeks after the treatment; while patients treated both topically and orally experienced menstruation within the treatment period itself. This result was in contrast to a group of patients not treated whose frequency of menstruation was random and irregular.

A composition of the present invention was tested for effectiveness in relieving of inflammation and/or pain associated with inflammatory dermatoses such as eczema, urticaria, psoriasis, erythema multiforme, and lichen planus;

inflammation of the gums (also known as gingivitis); and pain associated with acute injury/accident. This was a one-application, randomized study conducted in 145 patients: 75 of whom were afflicted with various inflammatory dermatoses most notably consisting of eczema or psoriasis, 35 of whom had gingivitis and 35 of whom had chronic pain from impact derived from an injury.

With respect to subjects afflicted with inflammatory dermatoses and gingivitis, pain and inflammation were assessed in the morning upon subject's awakening (baseline), and 24 hours after application. Analgesic response was determined using the sum of pain intensity differences (SPID), and medical examinations to evaluate inflammation based on degree of swelling and discoloration (redness). The composition was significantly superior to the placebo in improving SPID, and relieving inflammation. With respect to subjects afflicted with chronic pain derived from sudden impact, pain, stiffness and/or inflammation were also assessed in the morning upon subject's awakening, and 24 hours, 48 hours and 72 hours after application. Analgesic response was determined using the sum of pain intensity differences (SPID), the sum of stiffness intensity differences (SSID), and when appropriate, medical examinations. Once again, the composition was significantly superior to the placebo in improving SPID, SSID and relieving inflammation.

The details of the testing were as follows.

Of the 75 subjects, only subjects already diagnosed with inflammatory dermatoses such as eczema, urticaria, psoriasis, erythema multiforme, and lichen planus on their arms, volar and forearm areas and morning pain were accepted. 40 of these subjects had eczema, 30 had psoriasis and the remaining 5 had either urticaria, erythema multiforme or lichen planus. These subjects consistently experienced characteristic dermatosis and pain and were likely to be better able to detect, quantify and measure changes in their pain. Of the 35 subjects with gingivitis, only those subjects with dental records diagnosing them with periodontal disease were accepted. Of the 35 subjects who had chronic pain from impact derived from an injury, only those subjects who had experienced pain for at least 2 years in the same localized area generated from sudden impact such as an accident or injury were accepted. These subjects were required to suffer from morning pain and stiffness. Inflammation of the area often accompanied these symptoms.

All subject considered for enrollment stated on their screening forms that they were told by their personal physicians that they had the relevant affliction. Subjects were enrolled in the study only if the study's examining physician also determined upon physical examination that they had the relevant disorder. 67 subjects were rejected by the study physician at screening for not meeting the criteria's for the disorders. Approximately 48% of all subject were receiving active treatment for their conditions. To participate in this study, subjects had to be willing to discontinue use of medications for analgesia or inflammation for at least 7 days before applying the treatment. Only subjects who could make the required clinic visits, who the investigator believed were mentally competent to carry out the study procedure, and whose symptoms of severity was appropriate for treatment were enrolled in the study.

Before the study was begun, a medical history was obtained and a physical examination conducted on all subjects. Treatment was dispensed to the subjects as follows:

(A) With respect to those 75 subject afflicted with various inflammatory dermatoses (most notably consisting of eczema or psoriasis), subjects were instructed to rate the pain and inflammation in their arms immediately upon awakening. Then they were to apply the treatment by placing their arms in an aqueous solution consisting of 0.5 lb of grounded product and distilled water for a period of 45 minutes. After the treatment, subjects were to rate the pain and inflammation on a scale of 1 to 5 24 hours later. They were to refrain from washing the treated area during this time. Subjects were told specifically not to proceed with the study procedure unless they had at least moderate baseline pain (a 3 on the scale of 1 to 5). The requirement of at least moderate pain was deemed necessary for subjects to be able to detect and measure a change in pain level. The primary effectiveness variables as stated in the protocol were relief of pain and inflammation in the arm.

(B) Similarly, with respect to those 35 subjects with chronic pain from impact derived from an injury, subjects were instructed to rate the pain and inflammation in the afflicted area immediately upon awakening. Then they were to apply the localized are with an aqueous solution consisting of 0.5 lb of grounded product and distilled water for a period of 45 minutes. After the treatment, subjects were to rate the pain, stiffness and inflammation on a scale of 1 to 5 24 hours later, after which a second treatment was immediately applied and subjects rated the pain, stiffness and inflammation on the same scale and second time 48 hours after the initial rating. A final treatment was then immediately applied 72 hours after in the initial rating and a final rating of pain, stiffness and/or inflammation was assessed after this last (third) application. Subjects were to refrain from washing the treated area in the interim period between each individual rating and treatment. Subjects were told specifically not to proceed with the study procedures unless they had at lest moderate baseline pain (a 3 on a scale of 1 to 5). The requirement of at least moderate pain was deemed necessary for subjects to be able to detect a measure of change in pain level. The primary effectiveness variables as stated in the protocol were relief of pain or sensation of restricted motion and inflammation in the localized area.

(C) With respect to those 35 subjects with gingivitis, pain and inflammation were assessed in the morning upon subject's awakening (baseline), and 24 hours later (12 hours after application). Subjects were to apply 1 oz of product in 1 oz of distilled water by massaging the gum area for exactly 4 minutes that evening before sleeping. They were to refrain from rinsing after application. After the treatment, subjects were to rate the pain and inflammation on a scale of 1 to 5 12 hours later. Once again, subjects were told specifically not to proceed with the study procedure unless they had at least moderate baseline pain (a 3 on a scale of 1 to 5). The requirement of at least moderate pain was deemed necessary for subjects to be able to detect and measure change in pain level. The primary effectiveness variables as stated in the protocol were relief of pain and inflammation in the gums. With respect to each of the three treatment groups, a final medical examination was conducted by the study physician on each subject individually approximately 24 hours after the last treatment was applied.

All 145 subjects completed the study. The demographic and background characteristics of the subject population were unremarkable. There were no clinically important differences between or within treatment groups. Pain relief (a decrease in pain intensity) and inflammation relief (a decrease in inflammation severity) were the primary effectiveness variables. On the basis of SPID derived from the pain scores, SSID derived from the sensation of stiffness scores, and the final medical examination conducted on each subject by the study physician, the composition significantly reduced pain intensity and inflammation severity.

Of the 175 subjects with inflammation dermatoses, 23 had rated their pain at a level of 3, 33 at a level of 4, and 19 at a level of 5. About 69% of these subjects rated their pain at a level of 1 or 2, with all 23 subjects with an initial pain self-rating level of 3, resulting in a rating of 1 post treatment. Similarly, inflammation degrees declined significantly at least 2 points in every case. Most very severe (5) and severe (4) cases became mild (2) or moderate (3). 30% of subjects reporting a 3 or above rated their inflammation "none" (1) post treatment. The study physician confirmed the subjects' ratings with respect to inflammation using standard scales of redness and swelling.

With respect to those 35 patients with chronic pain from impact derived from an injury, 31 subjects had rated their pain at level 5, and 4 had rated their pain at a level 4. Out of the 31 subjects who had rated their pain as very severe, 21 rated their pain after the three treatments at 2 or moderate, and the remaining 10 rated their pain at 1 or none. The 4 subjects with an initial level 4 pain rating experienced a level 2 rating each after the three treatments. 26 subjects rated their stiffness at a level 4. Among these, 24 rated stiffness at 1 post treatment, 1 rated stiffness at 2 post treatment, and 1 rated stiffness at 3 post treatment. 9 subjects had initially rated their stiffness at level 5. Among these, 3 subjects rated their stiffness at 3 post treatment, 4 rated their stiffness at 2 post treatment, and 2 rated their stiffness at 1 post treatment. Similarly, in 34.3% of cases reporting inflammation, 20% experienced a reduction by 1 level, and the remainder reported a reduction of inflammation by 2 levels.

Of the 35 subjects suffering from gingivitis, 30 initially rated their pain at 4, and 5 initially rated their pain at 3. 33 subjects rated their pain post treatment at 2 including the 5 with an initial pain rating of 3, and the remaining 3 subjects rated their pain at 1 post treatment. The study physician noted a one level decrease in inflammation rating in about 57% of these cases, and a two level decrease in inflammation rating in the remaining subjects.

This invention has been described in detail with particular reference to certain preferred embodiments thereof, but it will be understood that variations and modifications can be effected within the spirit and scope of the invention.

What is claimed is:

1. A method for the relief of inflammation and/or pain in a mammal comprising:
    topically administering to said mammal in need of such treatment a therapeutically effective amount of a composition sufficient to induce alleviation of signs, symptoms or causes of inflammatory dermatosis, gingivitis and acute injury comprising:
    of from about 300 to about 1500 grams of a finely divided powder of safflower seeds having a particle size of 100 microns or less in about 6 to 7 gallons of water.

2. The method of claim 1 wherein said inflammatory dermatosis is eczema, urticaria, psoriasis, erythema multiforme and lichen planus.

3. A method for the relief of inflammation and/or pain in a mammal comprising:
    topically administering to said mammal in need of such treatment a therapeutically effective amount of a composition sufficient to induce alleviation of signs, symptoms or causes of inflammatory dermatosis, gingivitis and acute injury the composition comprising:
    an extract of safflower seeds, said extract prepared by:
        separating safflower seeds of their shell;
        comminuting the shelled safflower seeds to particle size of 100 micron or less to obtain a fine particle size powder;
        mixing the fine particle size powder with a solvent selected from the group consisting of acetone, methylethylketone, diethylketone, methanol and ethanol to dissolve soluble compounds from the fine particle size powder to obtain an extract thereof,
        separating the extract from the unsolvated fibrous material by filtration and discarding the unsolvated fibrous material;
        separating the extract from said solvent by evaporation or distillation to obtain said extract of said safflower seeds; and
        combining about 5 to 10 parts of said extract with about 1 to 3 parts of a pharmaceutically acceptable carrier selected from the group consisting of water, lotion, cream, paste, ointment, gel and a film-forming polymeric material.

4. The method of claim 3 wherein said inflammatory dermatosis is eczema, urticaria, psoriasis, erythema multiforme and lichen planus.

5. The method of claim 3, wherein said film-forming material is an anionic polymer having the formula:

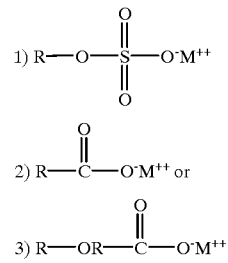

wherein
R is a paoymeric chain or residue;

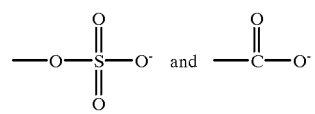

are anionic ligands; and
M is a divalent cation of $Mg^{++}$, $Ca^{++}$, $Zn^{++}$.

6. The method of claim 3 wherein said anionic polymer is selected from the group consisting of:
    sulfated polysaccharides;
    carboxylated polysaccharides;
    cellulose derivatives; and
    sulfated, sulfonated or carboxylated synthetic polymers.

7. The method of claim 6 wherein said carboxylated polysaccharide is pectin, algin or karaya gum.

8. The method of claim 6 wherein said cellulose derivative is ethylcellulose sulfate, sodium cellulose acetate sulfate and sodium carboxymethyl cellulose.

9. The method of claim 3 wherein said film-forming material is a cationic polymer having the formula:

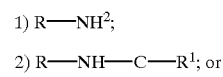

-continued

3) 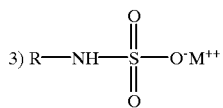

wherein

R is a sugar residue;

$R^1$ is $CH_3$ or $C_2H_5$, and $M^{++}$, is $Mg^{++}$, $Ca^{++}$, $Zn^{++}$ or $Ba^{++}$.

10. The method of claim 9 wherein said polymer is chondrotoin sulfate, dermatan sulfate, keratosulfate, hyaluronic acid, heparin and chitin.

11. The method of claim 3 wherein said film-forming material is a neutral polymer selected from the group consisting of polysaccharides, cellulose derivatives and synthetic polymers.

12. The method of claim 11 wherein said cellulose derivative is methylcellulose, hydroxyethylcellulose, ethylhydroxyethyl cellulose and hydroxypropyl cellulose.

13. The method of claim 11, wherein said synthetic polymer is polyvinylpyrrolidone, polyvinyl alcohol and the ethylene oxide polymers.

* * * * *